US008673945B2

(12) United States Patent
Woo et al.

(10) Patent No.: US 8,673,945 B2
(45) Date of Patent: Mar. 18, 2014

(54) SOLID PHARMACEUTICAL COMPOSITION COMPRISING AMLODIPINE AND LOSARTAN

(75) Inventors: Jong Soo Woo, Suwon-si (KR); Jae Hyun Park, Suwon-si (KR); Young Il Kim, Suwon-si (KR); Kyeong Soo Kim, Suwon-si (KR); Ho Taek Yim, Yongin-si (KR); Ji Hyun Im, Suwon-si (KR)

(73) Assignee: Hanmi Science Co., Ltd, Hwaseong-Si (KR)

( * ) Notice: Subject to any disclaimer, the term of this patent is extended or adjusted under 35 U.S.C. 154(b) by 321 days.

(21) Appl. No.: 13/140,348

(22) PCT Filed: Dec. 28, 2009

(86) PCT No.: PCT/KR2009/007829
§ 371 (c)(1),
(2), (4) Date: Jun. 16, 2011

(87) PCT Pub. No.: WO2010/085047
PCT Pub. Date: Jul. 29, 2010

(65) Prior Publication Data
US 2011/0251245 A1 Oct. 13, 2011

(30) Foreign Application Priority Data
Jan. 23, 2009 (KR) .................. 10-2009-0005840
Sep. 24, 2009 (KR) .................. 10-2009-0090540

(51) Int. Cl.
*A61K 31/41* (2006.01)
*A61K 31/44* (2006.01)
(52) U.S. Cl.
USPC ........................... 514/356; 514/381

(58) Field of Classification Search
USPC ................................. 514/356, 381
See application file for complete search history.

(56) References Cited

U.S. PATENT DOCUMENTS

| 6,677,356 | B1 | 1/2004 | Sethi et al. |
| 2002/0068740 | A1 | 6/2002 | Mylari |
| 2002/0099046 | A1 | 7/2002 | Scott |
| 2008/0050432 | A1 | 2/2008 | Jun et al. |
| 2008/0241240 | A1 | 10/2008 | Kim et al. |
| 2010/0233261 | A1 | 9/2010 | Woo et al. |

FOREIGN PATENT DOCUMENTS

| KR | 2008-0018841 A | 2/2008 |
| KR | 2008-0052852 A | 6/2008 |
| WO | 03/035046 A2 | 5/2003 |
| WO | 03/097045 A1 | 11/2003 |
| WO | 2005/070463 A2 | 8/2005 |

(Continued)

OTHER PUBLICATIONS

Rednic et al., Drug Development and Industrial Pharmacy, 1980;6(3):291-309.*

(Continued)

*Primary Examiner* — San-Ming Hui
(74) *Attorney, Agent, or Firm* — Sughrue Mion, PLLC

(57) ABSTRACT

The present invention relates to a solid pharmaceutical composition for preventing or treating cardiovascular disorders comprising amlodipine and losartan as active ingredients, and a disintegrant which is a mixture of at least two components selected from the group consisting of sodium starch glycolate, crosscarmellose sodium, and crosspovidone, which exhibits a high and stable level of amlodipine and losartan dissolution rates.

7 Claims, 2 Drawing Sheets

(56) References Cited

FOREIGN PATENT DOCUMENTS

| WO | 2006/048208 | A1 | 5/2006 |
|----|-------------|----|--------|
| WO | 2007/056324 | A2 | 5/2007 |
| WO | 2008/044862 | A1 | 4/2008 |
| WO | 2008/069612 | A1 | 6/2008 |

OTHER PUBLICATIONS

European Patent Office, European Search Report issued in corresponding EP Application No. 09838943.9, dated Jun. 27, 2012.
Chinese Patent Office, Chinese Office Action issued in corresponding CN Application No. 200980155067.X, dated Aug. 3, 2012.
New Zealand Patent Office, New Zealand Examination Report issued in corresponding NZ Application No. 594739, dated May 23, 2012.
Costa Rican Patent Office, Costa Rican Opposition issued in corresponding CR Application No. 2011-0450, dated Feb. 22, 2012.
Costa Rican Patent Office, Costa Rican Opposition issued in corresponding CR Application No. 2011-0449, dated Feb. 22, 2012.
Costa Rican Patent Office, Costa Rican Opposition issued in corresponding CR Application No. 2011-0448, dated Feb. 22, 2012.
Gohel et al., "Improving the Tablet Characteristics and Dissolution Profile of Ibuprofen by Using a Novel Coprocessed Superdisintegrant: A Technical Note," AAPS PharmSciTech, 2007, vol. 8, No. 1, pp. E1-E6.
Colombian Patent Office, Colombian Office Action issued in corresponding CO Application No. 11-105492, dated May 6, 2013.

\* cited by examiner

SOLID PHARMACEUTICAL COMPOSITION COMPRISING AMLODIPINE AND LOSARTAN

FIELD OF THE INVENTION

The present invention relates to a solid pharmaceutical composition for preventing or treating cardiovascular disorders comprising amlodipine and losartan, which can maintain a high and stable level of amlodipine and losartan dissolution rates even under a low pH condition.

BACKGROUND OF THE INVENTION

In the treatment of hypertension to reduce the risks of complications such as coronary heart diseases and cardiovascular diseases, e.g., stroke, heart failure, and myocardial infarction, it is more important to maintain the blood pressure within a normal range on a consistent basis than to simply lower the blood pressure level itself. Accordingly, antihypertensive agents are required to be effective for long-term treatment of hypertension. Further, advanced therapy using a combination of two or more drugs having different pharmacological actions makes it possible to improve preventive or therapeutic effects, while lowering side effects arising from the long term administration of a single drug.

Notable antihypertensive drugs include diuretics, sympatholytic agents, and vasodilators. Vasodilators are most widely prescribed antihypertensive drugs, and they are divided into several groups according to their pharmacological actions which include ACE (angiotensin converting enzyme) inhibitors, angiotensin II receptor antagonists, and calcium channel blockers.

Amlodipine is the generic name for 3-ethyl-5-methyl-2-(2-aminoethoxy-methyl)-4-(2-chlorophenyl)-6-methyl-1,4-dihydro-3,5-pyridine dicarboxylate. Amlodipine besylate is currently marketed as Novasc (trade mark). Amlodipine is a long-acting calcium channel blocker which is useful in treating cardiovascular disorders such as agina, hypertension, and congestive heart failure.

Losartan is the generic name for 2-butyl-4-chloro-1-[[2'-(1H-tetrazol-5-yl)[1,1'-biphenyl]-4-yl]methyl]-1H-imidazol-5-methanol, which has been disclosed in U.S. Pat. Nos. 5,608,075; 5,138,069; and 5,153,197. Losartan potassium is commercially available as Cozaar (trade mark). Losartan blocks the interaction of angiotensin II and its receptor, and is mainly used for treating hypertension, heart failure, ischemic peripheral circulatory disorder, myocardial ischemia (angina pectoris), diabetic neuropathy, and glaucoma, and also for preventing the progression of post-myocardial infarction heart failure.

The present inventors have found that a combined formulation which comprises amlodipine and losartan having different pharmacological activities is useful for treating hypertension, and have conducted intensive studies on such a combined formulation.

However, when the combined formulation of amlodipine and losartan is prepared by simply mixing the two drugs, undesirable gelation of losartan occurs: Losartan readily dissolves in purified water and is easily released at a relatively high pH (e.g., pH 6.8), but it is very slowly released at a low pH (e.g., pH 2.0 or pH 1.2) because of the gelation. In case Cozaar (trade mark), a commercially available losartan preparation is used, the amount of losartan released over the initial 30 minutes is less than 30% at a pH range of 1.2 to 2.0. In such combined formulation of amlodipine and losartan, amlodipine may also be locked in the losartan gel.

An orally administered preparation generally undergoes disintegration and dissolution in the stomach having a low pH, and therefore, a low dissolution rate at a low pH of an active ingredient in a preparation can result in significant lowering of its bioavailability.

In addition, considering the fact that the pH in the stomach of a normal adult varies widely in a range of 1.0 to 3.5 and $C_{max}$ of losartan after food ingestion becomes reduced by about 10%, development on such an amlodipine-losartan combined formulation capable of maintaining a relatively constant dissolution rate at such pH variation in the stomach is needed.

SUMMARY OF THE INVENTION

Accordingly, it is an object of the present invention to provide a solid pharmaceutical composition containing amlodipine and losartan, which exhibits minimal fluctuation in the dissolution rates of the active ingredients with pH variation, i.e., a high and stable level of amlodipine and losartan dissolution rates even under a low pH condition.

In accordance with one aspect of the present invention, there is provided a solid pharmaceutical composition for preventing or treating cardiovascular disorders comprising amlodipine and losartan as active ingredients, and a disintegrant which is a mixture of at least two components selected from the group consisting of sodium starch glycolate, crosscarmellose sodium, and crosspovidone.

BRIEF DESCRIPTION OF THE DRAWINGS

The above and other objects and features of the present invention will become apparent from the following description of the invention, when taken in conjunction with the accompanying drawings which show.

DETAILED DESCRIPTION OF THE INVENTION

Figure 1:
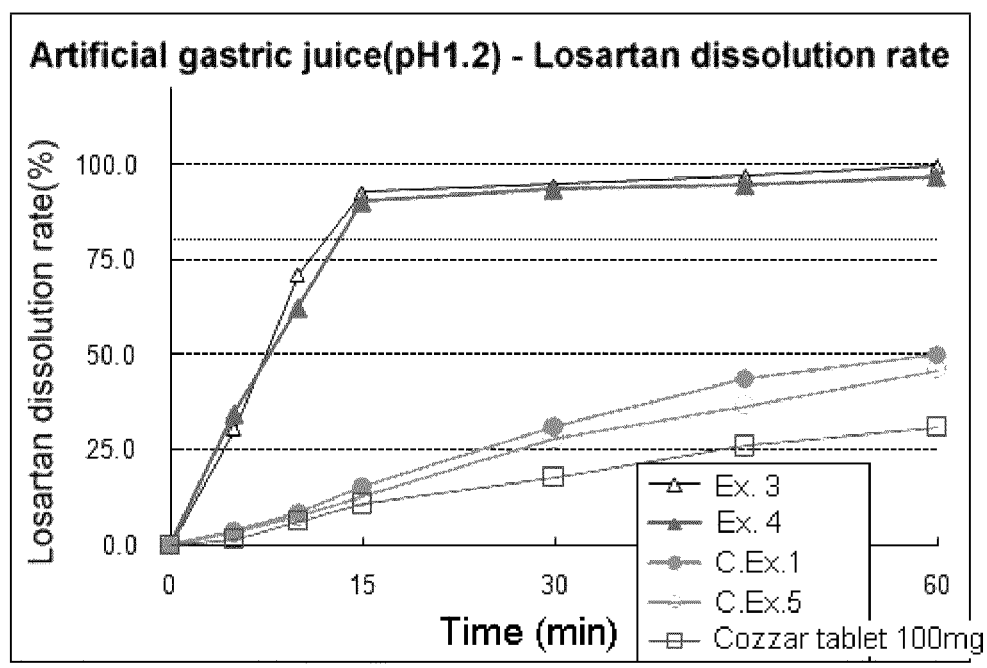
FIGS. 1 and 2: losartan dissolution rates in an artificial gastric juice (pH 1.2) and in 0.01N HCl (pH 2.0) observed for the combined tablets prepared in Examples 3 and 4, and Comparative Examples 1 and 5, and Cozaar tablet (trade mark) (Test Example 2), respectively.

The solid pharmaceutical composition of the present invention comprising amlodipine and losartan active ingredients as well as at least two specific disintegrants selected from sodium starch glycolate, crosscarmellose sodium, and crosspovidone exhibits high amlodipine and losartan dissolution rates at a wide range of pH while exhibiting a sufficient structural strength when formulated.

Losartan used in the present invention may be one of various forms of pharmaceutically acceptable salts. In one embodiment, the pharmaceutically acceptable salt of losartan is losartan potassium.

In one embodiment, based on a unit formulation (solid administration form), losartan potassium is conventionally used in an amount ranging from about 10 to about 500 mg. In another embodiment, losartan potassium is conventionally used in an amount ranging from about 25 to about 250 mg. In another embodiment, losartan potassium is conventionally used in an amount ranging from about 50 to about 200 mg. In another embodiment, losartan potassium is conventionally used in an amount ranging from about 50 to about 100 mg.

Amlodipine used in the present invention may be one of various forms of pharmaceutically acceptable salts. The pharmaceutically acceptable salts of amlodipine include hydrochloride, hydrobromide, sulphate, phosphate, acetate, maleate, fumarate, lactate, tartrate, citrate, gluconate, besylate, and camsylate salts, but are not limited thereto. In one embodiment, the pharmaceutically acceptable salt of amlodipine is amlodipine besylate or amlodipine camsylate. Also, amlodipine used in the present invention may be racemic amlodipine or S-amlodipine.

In one embodiment, based on a unit formulation (solid administration form), amlodipine is conventionally used in an amount ranging from about 1.25 to about 20 mg. In another embodiment, amlodipine is conventionally used in an amount ranging from about 1.875 to about 15 mg. In another embodiment, amlodipine is conventionally used in an amount ranging from about 2.5 to about 10 mg. In another embodiment, amlodipine is conventionally used in an amount ranging from about 5 to about 10 mg. The prescribed amount of amlodipine means an amount of free amlodipine present in a corresponding solid administration form.

The inventive composition comprises pharmaceutically acceptable additives suitable for a desired amlodipine-losartan combined, solid administration formulation, in particular, critically comprises a specific disintegrant among them. In this regard, the present inventors have found that the dissolution rates of amlodipine and losartan significantly depend on the kind and the number of used disintegrants, especially, at a low pH. Accordingly, the present invention provides a solid pharmaceutical composition having the specific kind and number of disintegrants which is capable of exhibiting optimized dissolution rates.

Referred to as the "disintegrant" are materials which function to accelerate disintegration of a solid composition in a digestive juice, thereby enhancing the dissolution rate of an active ingredient incorporated therein. Meanwhile, excessive use of the disintegrant does not allow a high strength of the solid preparation which makes its shape maintained during its manufacturing, packaging, transportation or storage process. That is, it is very important to use a suitable kind of a disintegrant in a suitable amount so as to enhance a solubility of a solid preparation, especially a tablet, without causing undesirable structural deformation.

In one embodiment, the disintegrant used in the present invention is a mixture of at least two components selected from the group consisting of sodium starch glycolate, crosscarmellose sodium, and crosspovidone. In another embodiment, the disintegrant is a mixture of sodium starch glycolate and crosspovidone. In another embodiment, the disintegrant is a mixture of sodium starch glycolate and crosscarmellose sodium. In one embodiment, the disintegrant may be used in an amount ranging from about 2.5 to about 30% by weight based on the total weight of the composition. In another embodiment, the disintegrant may be used in an amount ranging from about 5 to about 15% by weight based on the total weight of the composition.

The present inventors have found that the combination of two or more components among the afore-mentioned three components leads to a desirable structural strength and dissolution aspect of an amlodipine-losartan combined formulation. Further, through such a technique as mentioned above, the present invention achieves reduction in the total used amount of the disintegrant, which results in improvement in tableting capability. When sodium starch glycolate, crosscarmellose sodium or crosspovidone is used in a single, although its amount is excessive, retardation of dissolution due to the gelation of losartan is not effectively inhibited, and it is frequently hard to formulate into an oral administration form due to an unsatisfactory compression force and a high abrasion degree.

The pharmaceutically acceptable additives may include diluents such as microcrystalline cellulose, lactose, mannitol, sodium citrate, calcium phosphate, glycine, starch, and a mixture thereof. In one embodiment, the diluent may be used in an amount ranging from about 15 to about 90% by weight based on the total weight of the composition. In another embodiment, the diluent may be used in amount ranging from about 30 to about 70% by weight based on the total weight of the composition.

Besides the diluents, the pharmaceutically acceptable additives may include stabilizing agents, binders, and lubricants.

In one embodiment, the stabilizing agent used in the present invention may be an anti-oxidant. The use of an anti-oxidant enhances stabilities of active ingredients against the undesirable reaction with other pharmaceutically acceptable additives during a blending process and against deformation by heat or moisture with time, resulting in significant increase of stability of the amlodipine-losartan combined formulation.

Representative examples of the anti-oxidant used in the present invention include butylated hydroxytoluene (BHT), butylated hydroxyanisole (BHA), ascorbic acid, ascorbyl palmitic acid, ethylene diamine tetracetic acid (EDTA), sodium pyrosulfite, and a mixture thereof. In one embodiment, the anti-oxidant is butylated hydroxytoluene.

Representative examples of the binder used in the present invention include hydroxypropylcellulose (HPC), hydroxypropylmethylcellulose (HPMC), polyvinylpyrrolidone, macrogol, silicate derivatives such as hard silica, synthesized aluminum silicate, calcium silicate, and magnesium metasilicate aluminate, phosphates such as calcium monohydrogen phosphate, carbonates such as calcium carbonate, and a mixture thereof.

Representative examples of the lubricant used in the present invention include stearic acid, metal stearate such as calcium stearate and magnesium stearate, talc, colloidal silica, saccharose fatty acid esters, hydrogen-added vegetable oils, waxes having a high melting point, glyceryl fatty acid esters, glycerol dibehenate, and a mixture thereof.

The inventive composition comprising the amlodipine and losartan can provide improved preventive or therapeutic effects for cardiovascular disorders such as angina pectoris, hypertension, artery vasospasm, deep vein, cardiac hypertrophy, cerebral infarct, congestive heart failure and myocardial infarction.

The inventive composition may be administered in the form of a tablet, a capsule or multi-particles through various routes of oral administration including oral cavity, mouth and hypoglossus. In one embodiment, the inventive composition may be formulated into the tablet form and orally administered. The inventive composition may be easily formulated into the tablet form by way of mixing constituents and tableting them together.

In one embodiment, such a tablet obtained from the inventive composition may have an outer coating layer. The tablet should have a suitable hardness, i.e., an average hardness ranging from 5 kp to 30 kp when measured before formation of an optional outer coating layer.

The coating layer may consist of any one of conventional high molecular compounds which are capable of forming the film coating. The amount of the coating should be reduced to a minimum for easy administration and manufacturing efficiency, and it may be in a range of about 1 to about 10% by weight based on the total weight of the formulation. In another embodiment, it may be in a range of about 3 to about 5% by weight based on the total weight of the formulation.

The following Examples are intended to further illustrate the present invention without limiting its scope.

Example 1

Preparation of Combined Tablet—(I)

| - Mixing part - | |
|---|---|
| losartan potassium | 100.0 mg |
| amlodipine camsylate | 7.84 mg (amlodipine 5 mg) |
| microcrystalline cellulose | 250.0 mg |
| mannitol | 63.16 mg |
| sodium starch glycolate | 15.0 mg |
| crosspovidone | 15.0 mg |
| polyvinylpyrrolidone | 5.0 mg |
| - Lubricant - | |
| magnesium stearate | 4.0 mg |

Losartan potassium, amlodipine camsylate, microcrystalline cellulose, mannitol, sodium starch glycolate, crosspovidone, and polyvinylpyrrolidone were each passed through a #20 mesh and mixed in a V-type mixer for 30 mins. Subsequently, an appropriate amount of magnesium stearate (lubricant) was added thereto, mixed for 5 mins, and the resulting mixture was subjected to tableting with an compression force of about 20 kN using a rotary tableting machine (Sejong Pharmatek, MRC-45) to prepare a losartan 100 mg-amlodipine 5 mg combined tablet.

An average hardness and an abrasion degree of the tablet thus obtained were 19.7 kp and 0.1%, respectively, when measured using Erweka hardness and abrasion measuring instruments (25 rpm, 100-times free falling), which suggests that a strength of the tablet is good.

Example 2

Preparation of Combined Tablet—(II)

A combined tablet was prepared by repeating the procedure of Example 1 except for using 15 mg of crosscarmellose sodium instead of 15 mg of crosspovidone. An average hardness and an abrasion degree of the tablet thus obtained were 18.5 kp and 0.0%, respectively, which suggests that a strength of the tablet is good.

Example 3

Preparation of Combined Tablet—(III)

A combined tablet was prepared by repeating the procedure of Example 1 except for using each of sodium starch glycolate and crosspovidone in an amount of 25 mg. An average hardness and an abrasion degree of the tablet thus obtained were 15.3 kp and 0.2%, respectively, which suggests that a strength of the tablet is good.

Example 4

Preparation of Combined Tablet—(IV)

A combined tablet was prepared by repeating the procedure of Example 1 except for using sodium starch glycolate in an amount of 25 mg while using 25 mg of crosscarmellose sodium instead of 15 mg of crosspovidone. An average hardness and an abrasion degree of the tablet thus obtained were 14.5 kp and 0.1%, respectively, which suggests that a strength of the tablet is good.

Example 5

Preparation of Combined Tablet—(V)

A combined tablet was prepared by repeating the procedure of Example 1 except for using crosspovidone in an amount of 25 mg while using 25 mg of crosscarmellose sodium instead of 15 mg of sodium starch glycolate. An average hardness and an abrasion degree of the tablet thus obtained were 17.1 kp and 0.1%, respectively, which suggests that a strength of the tablet is good.

Example 6

Preparation of Combined Tablet—(VI)

A combined tablet was prepared by repeating the procedure of Example 1 except for using each of sodium starch glycolate and crosspovidone in an amount of 25 mg while further using crosscarmellose sodium in an amount of 25 mg. An average hardness and an abrasion degree of the tablet thus obtained were 11.7 kp and 0.3%, respectively, which suggests that a strength of the tablet is good.

Example 7

Preparation of Combined Tablet—(VII)

A combined tablet was prepared by repeating the procedure of Example 1 except for using each of sodium starch glycolate and crosspovidone in an amount of 40 mg. An average hardness and an abrasion degree of the tablet thus obtained were 11.2 kp and 0.2%, respectively, which suggests that a strength of the tablet is good.

Example 8

Preparation of Combined Tablet—(VIII)

A losartan 50 mg-amlodipine 5 mg combined tablet was prepared by repeating the procedure of Example 1 except for using losartan potassium in an amount of 50 mg. An average hardness and an abrasion degree of the tablet thus obtained were 16.9 kp and 0.3%, respectively, which suggests that a strength of the tablet is good.

Comparative Example 1

Preparation of Combined Tablet—(IX)

| - Mixing part - | |
|---|---|
| losartan potassium | 100.0 mg |
| amlodipine camsylate | 7.84 mg (amlodipine 5 mg) |
| microcrystalline cellulose | 250.0 mg |
| mannitol | 63.16 mg |
| sodium starch glycolate | 40.0 mg |
| polyvinylpyrrolidone | 5.0 mg |
| - Lubricant - | |
| magnesium stearate | 4.0 mg |

A losartan 100 mg-amlodipine 5 mg combined tablet was prepared by repeating the procedure of Example 1 using the specific constituents as shown above. An average hardness and an abrasion degree of the tablet thus obtained were 14.3 kp and 0.3%, respectively, which suggests that a strength of the tablet is good.

Comparative Example 2

Preparation of Combined Tablet—(X)

A combined tablet was prepared by repeating the procedure of Comparative Example 1 except for using sodium starch glycolate in an amount of 80 mg. An average hardness and an abrasion degree of the tablet thus obtained were 4.7 kp and 1.2%, respectively, which suggests that a strength of the tablet is insufficient and poor.

Comparative Example 3

Preparation of Combined Tablet—(XI)

A combined tablet was prepared by repeating the procedure of Comparative Example 1 except for using 40 mg of crosscarmellose sodium instead of 40 mg of sodium starch glycolate. An average hardness and an abrasion degree of the tablet thus obtained were 12.5 kp and 0.2%, respectively, which suggests that a strength of the tablet is good.

Comparative Example 4

Preparation of Combined Tablet—(XII)

A combined tablet was prepared by repeating the procedure of Comparative Example 1 except for using 40 mg of calcium carboxymethylcellulose instead of 40 mg of sodium starch glycolate. An average hardness and an abrasion degree of the tablet thus obtained were 14.9 kp and 0.2%, respectively, which suggests that a strength of the tablet is good.

Comparative Example 5

Preparation of Combined Tablet—(XIII)

A combined tablet was prepared by repeating the procedure of Comparative Example 1 except for using a mixture of 25 mg of calcium carboxymethylcellulose and 25 mg of corn starch instead of 40 mg of sodium starch glycolate. An average hardness and an abrasion degree of the tablet thus obtained were 15.3 kp and 0.1%, respectively, which suggests that a strength of the tablet is good.

Hereinafter, the compositions and properties (hardness and abrasion degree) of formulations obtained in Examples 1 to 8 and Comparative Examples 1 to 5 are shown in Table 1.

TABLE 1

| | Ex. 1 | Ex. 2 | Ex. 3 | Ex. 4 | Ex. 5 | Ex. 6 | Ex. 7 | Ex. 8 | C.E. 1 | C.E. 2 | C.E. 3 | C.E. 4 | C.E. 5 |
|---|---|---|---|---|---|---|---|---|---|---|---|---|---|
| Ratio of disintegrant (%) | 6.5 | 6.5 | 10.4 | 10.4 | 10.4 | 14.9 | 15.7 | 7.3 | 8.5 | 15.7 | 8.5 | 8.5 | 10.4 |
| (a) | 100 | 100 | 100 | 100 | 100 | 100 | 100 | 50 | 100 | 100 | 100 | 100 | 100 |
| (b) | 7.84 | 7.84 | 7.84 | 7.84 | 7.84 | 7.84 | 7.84 | 7.84 | 7.84 | 7.84 | 7.84 | 7.84 | 7.84 |
| (c) | 15 | 15 | 25 | 25 | — | 25 | 40 | 15 | 40 | 80 | — | — | — |
| (d) | 15 | — | 25 | — | 25 | 25 | 40 | 15 | — | — | — | — | — |
| (e) | — | 15 | — | 25 | 25 | 25 | — | — | — | — | 40 | — | — |
| (f) | — | — | — | — | — | — | — | — | — | — | — | 40 | 25 |
| (g) | — | — | — | — | — | — | — | — | — | — | — | — | 25 |
| (h) | 250 | 250 | 250 | 250 | 250 | 250 | 250 | 250 | 250 | 250 | 250 | 250 | 250 |
| (i) | 63.16 | 63.16 | 63.16 | 63.16 | 63.16 | 63.16 | 63.16 | 63.16 | 63.16 | 63.16 | 63.16 | 63.16 | 63.16 |
| (j) | 5 | 5 | 5 | 5 | 5 | 5 | 5 | 5 | 5 | 5 | 5 | 5 | 5 |
| (k) | 4 | 4 | 4 | 4 | 4 | 4 | 4 | 4 | 4 | 4 | 4 | 4 | 4 |
| Total weight (mg/tablet) | 460 | 460 | 480 | 480 | 480 | 505 | 510 | 410 | 470 | 510 | 470 | 470 | 480 |
| Hardness (kp) | 19.7 | 18.5 | 15.3 | 14.5 | 17.1 | 11.7 | 11.2 | 16.9 | 14.3 | 4.7 | 12.5 | 14.9 | 15.3 |
| Abrasion (%) | 0.1 | 0.0 | 0.2 | 0.1 | 0.1 | 0.3 | 0.2 | 0.3 | 0.3 | 1.2 | 0.2 | 0.2 | 0.1 |

(a) losartan potassium
(b) amlodipine camsylate
(c) sodium starch glycolate
(d) crosspovidone
(e) crosscarmellose sodium
(f) calcium carboxymethylcellulose
(g) corn starch
(h) microcrystalline cellulose
(i) mannitol
(j) polyvinylpyrrolidone
(k) magnesium stearate

Test Example 1

Dissolution Test of Amlodipine

The losartan-amlodipine combined tablets obtained in Examples 1 to 8 and Comparative Examples 1 to 5 were each subjected to a drug dissolution test under the following conditions. The results are shown in Table 2.

—Test Conditions—
Effluent: 900 ml of artificial gastric juice (pH 1.2)
Dissolution-test system: USP paddle method, 50 rpm
Temperature: 37° C.
—Analytical Conditions—
Column: stainless steel column (inner diameter: 4.6 mm, length: 15 cm) filled with octadecylsilanized silica gel for 5 μm liquid chromatography
Mobile phase: a mixture of methanol and 0.03M potassium dihydrogen phosphate (600:400, v/v)
Detector: ultraviolet spectrophotometer (350 nm)
Flow rate: 1.5 ml/min
Injection volume: 20 μl

TABLE 2

| | Ex. 1 | Ex. 2 | Ex. 3 | Ex. 4 | Ex. 5 | Ex. 6 | Ex. 7 | Ex. 8 | C.E. 1 | C.E. 2 | C.E. 3 | C.E. 4 | C.E. 5 |
|---|---|---|---|---|---|---|---|---|---|---|---|---|---|
| ① | 75.3 | 77.2 | 90.5 | 92.8 | 88.8 | 92.1 | 93.5 | 92.5 | 38.3 | 56.2 | 45.5 | 26.3 | 25.3 |
| ② | 90.9 | 90.2 | 95.1 | 99.4 | 96.2 | 95.9 | 98.1 | 99.0 | 52.1 | 75.4 | 68.4 | 40.2 | 41.5 |

① Dissolution rate of amlodipine at 30 min (%)
② Dissolution rate of amlodipine at 60 min (%)

As shown in Table 2, the amlodipine dissolution rates at 30 and 60 minutes of the combined tablets obtained in Examples 1 to 8 were 75% or more and 90% or more, respectively, while those obtained in Comparative Examples 1 to 5 exhibited even lower amlodipine dissolution rates. Especially, although the tablet obtained in Comparative Example 2 has a low hardness of 4.7 kp, its amlodipine dissolution rate at 30 minutes does not go beyond 60%.

Test Example 2

Dissolution Test of Losartan

Figure 2:
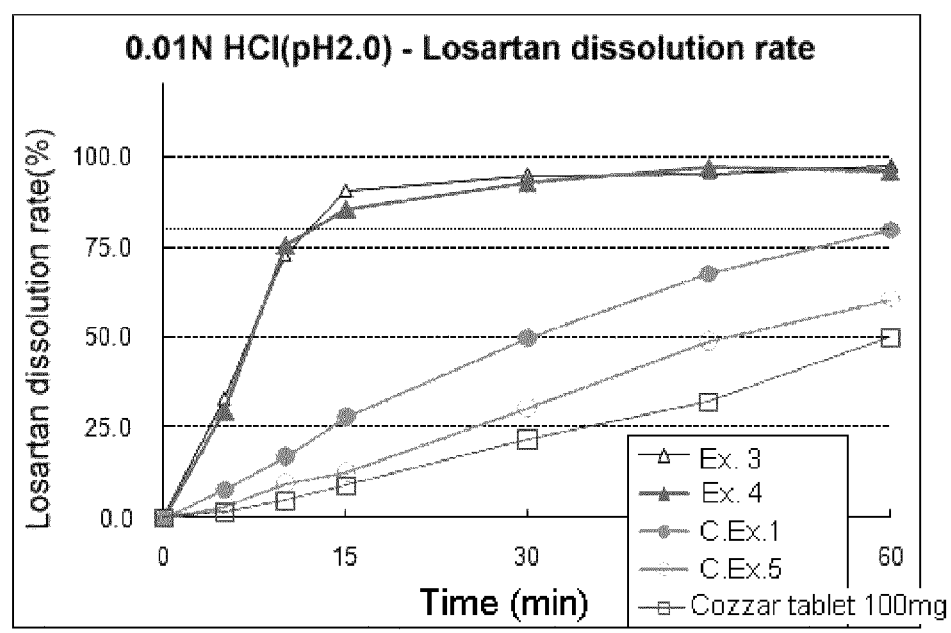

The combined tablets obtained in Examples 3 and 4, and Comparative Examples 1 and 5, and 100 mg of Cozaar tablet (trade mark) were each subjected to a drug dissolution test under the following conditions. The results are shown in FIGS. 1 and 2.

—Test Conditions—
Effluent: 900 ml of artificial gastric juice (pH 1.2) or 0.01 N HCl (pH 2.0)
Dissolution-test system: USP paddle method, 50 rpm
Temperature: 37° C.
—Analytical Conditions—
Column: stainless steel column (inner diameter: 4.6 mm, length: 15 cm) filled with octadecylsilanized silica gel for 5 μm liquid chromatography
Mobile Phase:
 mobile phase A—phosphate buffer:acetonitrile (850:150, v/v)
 mobile phase B—acetonitrile
 concentration gradient system

| Time (min) | Mobile phase A % | Mobile phase B % |
|---|---|---|
| 0 | 80 | 20 |
| 10 | 40 | 60 |
| 11 | 80 | 20 |
| 15 | 80 | 20 |

Detector: ultraviolet spectrophotometer (250 nm)
Flow rate: 1.5 ml/min
Injection volume: 10 μl
—Results—

The above dissolution-test system (USP paddle method, 50 rpm) is the most widely used to evaluate a dissolution rate of drug for the oral formulations, and the used effluent (the artificial gastric juice (pH 1.2) or 0.01 N HCl (pH 2.0)) has pH similar to that of the gastrointestinal tract.

As shown in FIGS. 1 and 2, the combined tablets obtained in Examples 3 and 4 exhibited even higher losartan dissolution rates than those of the tablets obtained in Comparative Examples 1 and 5, and Cozaar tablet (trade mark) which is a single formulation of losartan.

While the invention has been described with respect to the above specific embodiments, it should be recognized that various modifications and changes may be made to the invention by those skilled in the art which also fall within the scope of the invention as defined by the appended claims.

What is claimed is:

1. A solid pharmaceutical composition comprising amlodipine and losartan as active ingredients, and a disintegrant which is a mixture of at least two components selected from the group consisting of sodium starch glycolate, crosscarmellose sodium, and crosspovidone.

2. The composition of claim 1, wherein the disintegrant is a mixture of sodium starch glycolate and crosspovidone.

3. The composition of claim 1, wherein the disintegrant is a mixture of sodium starch glycolate and crosscarmellose sodium.

4. The composition of claim 1, wherein the disintegrant is used in an amount ranging from about 2.5 to about 30% by weight based on the total weight of the composition.

5. The composition of claim 4, wherein the disintegrant is used in an amount ranging from about 5 to about 15% by weight based on the total weight of the composition.

6. A method for treating cardiovascular disorders comprising administering the solid composition of claim 1 to a subject in need thereof.

7. The method of claim 6, wherein the cardiovascular disorders are selected from the group consisting of angina pectoris, hypertension, artery vasospasm, deep vein, cardiac hypertrophy, cerebral infarct, congestive heart failure, and myocardial infarction.

* * * * *